United States Patent [19]
Shuttleworth

[11] Patent Number: 5,214,186
[45] Date of Patent: May 25, 1993

[54] PROCESS FOR THE PREPARATION OF ARYLIDINE DYES USING AN ACTIVE METHYLENE COMPOUND

[75] Inventor: Leslie Shuttleworth, Webster, N.Y.

[73] Assignee: Eastman Kodak Company, Rochester, N.Y.

[21] Appl. No.: 801,224

[22] Filed: Dec. 3, 1991

[51] Int. Cl.$^5$ ............... C07C 255/00; C07C 211/00; C07C 209/00

[52] U.S. Cl. .................... 558/370; 558/373; 558/374; 558/375; 558/376; 558/400; 558/401; 558/402; 558/403; 564/305; 564/409

[58] Field of Search ............... 558/370, 373, 374, 375, 558/376, 403, 400, 401, 402; 564/305, 409

[56] References Cited

U.S. PATENT DOCUMENTS

| | | | |
|---|---|---|---|
| 2,594,309 | 4/1952 | Hitchings et al. | 558/375 X |
| 2,721,799 | 10/1955 | Edwards et al. | 558/370 X |
| 2,755,298 | 7/1956 | Whittaker | 558/375 |
| 2,774,783 | 12/1956 | Ardis | 558/403 X |
| 2,824,121 | 2/1958 | Nicholl et al. | 558/375 X |
| 3,076,015 | 1/1963 | McCall et al. | 558/375 X |
| 4,006,178 | 2/1977 | Stagi et al. | 558/403 X |

FOREIGN PATENT DOCUMENTS

| | | | |
|---|---|---|---|
| 41-19409 | 11/1966 | Japan | 558/375 |
| 41-20218 | 11/1966 | Japan | 558/375 |
| 53-149911 | 12/1978 | Japan | 558/375 |
| 53-149912 | 12/1978 | Japan | 558/375 |

OTHER PUBLICATIONS

Fieser et al., "Reagents for Organic Synthesis", vol. 5, p. 446 (1975).

*Initiating Carbenium Ions from Tetramethylene Zwitterions Cationic Polymerization Initiated by 2,2-Dicyanovinyl Iodide and 2,2-Dicyanovinyl p-Toluenesulfonate*, Polymer Bulletin—Springer-Verlag 1985; Anne Buyle Padias and H. K. Hall, Jr. Chemistry Department, University of Arizona, Tucson, Ariz. 85721, USA.

*The Chemistry of Synthetic Dyes*, Academic Press, N.Y., 1970, vol. III, p. 450; K. Venkataraman.

*Primary Examiner*—Floyd D. Higel
*Attorney, Agent, or Firm*—Gordon M. Stewart

[57] ABSTRACT

A process for the preparation of arylidene dyes comprises the reaction of an aromatic amine with an enolate salt of a formylated active methylene compound in the presence of a sulfonyl halide compound. An enol sulfonate is postulated as a reactive intermediate in the reaction. The process gives high yields of products under mild reaction conditions and allows the use of aromatic groups containing substituents such as hydroxy that lead to side reactions and low product yields with previously known methods for making arylidene dyes.

8 Claims, No Drawings

PROCESS FOR THE PREPARATION OF ARYLIDINE DYES USING AN ACTIVE METHYLENE COMPOUND

FIELD OF THE INVENTION

This invention relates to a novel process for the preparation of dyes and, more particularly, to the preparation of arylidene, or methine, dyes which have utility in photographic compositions, textile fibers, and other products as colorants, dyestuffs and the like.

BACKGROUND OF THE INVENTION

Arylidene, or methine, dyes are of the formula

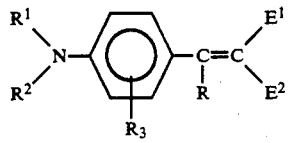

wherein R, $R^1$, and $R^2$ are hydrogen atoms, alkyl or cycloalkyl groups, or substituted alkyl or cycloalkyl groups, $R^3$ is a hydrogen atom, an alkyl or alkoxy group, a carbonylamino radical, or a fused phenyl ring, or $R^2$ and $R^3$ together form a ring, and $E^1$ and $E^2$ are strongly electron withdrawing unsaturated substituents.

Several methods are known for the preparation of arylidene dyes. In one of these methods an aromatic amine is formylated with a mixture of phosphoryl chloride and dimethylformamide in a Vilsmeier reaction. A description of this reaction is given in K. Venkataraman, *The Chemistry of Synthetic Dyes*, Academic Press, N.Y., 1970, Vol. III, p. 450. The aminosubstituted benzaldehyde produced in this step is next condensed with an active methylene compound to yield an arylidene dye.

This method of preparing arylidene dyes has severe limitations in that many aromatic amines undergo formylation in the Vilsmeier reaction poorly, with undesirable side reactions. For example, if aromatic amines have hydroxy or acetamido substituents, such groups undergo chlorination by the phosphorus oxychloride employed in the reaction. Similarly, anilines containing only one N-alkyl substituent yield undesirable side products under the conditions of the reaction.

U.S. Pat. No. 4,006,178 discloses the preparation of arylidene dyes containing dicyanovinyl substituents

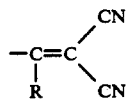

where R denotes a hydrogen atom or an alkyl, cycloalkyl, or aralkyl group. Dicyanovinyl substituted arylidene dyes are prepared by the reaction of an aromatic amine with a 1-halogeno-2,2-dicyanoethylene, preferably 1-chloro-2,2-dicyanoethylene. This latter compound can be prepared by several multistep procedures. One method, described in U.S. Pat. No. 2,774,783, starts with 1-acetoxy-1,1-dicyanoethane, which is pyrolyzed to yield 1,1-dicyanoethylene, which, without isolation, is chlorinated to 1,2-dichloro-1,1-dicyanoethane, which product is subjected to a second pyrolysis step to give 1-chloro-2,2-dicyanoethylene.

This process for the preparation of dicyanosubstituted arylidene dyes suffers from the disadvantage that the required reactant 1-chloro-2,2-dicyanoethylene must be prepared and isolated from a multistep process. Furthermore, in its reaction with an aromatic amine, hydrogen chloride is formed. This requires either that a 100% excess of the aromatic amine be employed to neutralize the generated acid or that a stoichiometric quantity of a more strongly basic amine, for example, triethylamine, be added under closely controlled conditions to neutralize the acid.

BRIEF SUMMARY OF THE INVENTION

The process of the invention produces arylidene, or methine, dyes of the formula

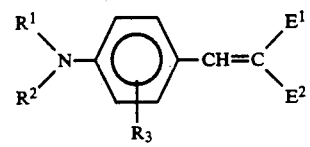

wherein $R^1$ and $R^2$ are hydrogen atoms, alkyl or cycloalkyl groups, or substituted alkyl or cycloalkyl groups, $R^3$ is a hydrogen atom, or an alkyl or alkoxy group, or a fused phenyl ring, or a carbonylamino radical such as alkanoylamino, aroylamino, aroylamino, alkoxycarbonylamino and aryloxycarbonylamino, or $R^2$ and $R^3$ together form a ring, and $E^1$ and $E^2$ are strongly electron-withdrawing unsaturated substituents that have Hammett sigma constants greater than +0.6 (J. Hine, *Physical Organic Chemistry*, 2nd ed., McGraw-Hill, N.Y., 1962, p. 90), such as cyano, acyl, carbamyl, alkoxycarbonyl, alkylsulfonyl and arylsulfonyl. In the process of the invention an active methylene compound of the formula

reacts with an alkyl formate in the presence of a strong base such as an alkali metal alkoxide or hydride to give an enolate salt of the formula.

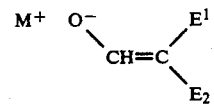

wherein $M^+$ represents an alkali metal ion, said enolate salt further reacting with an aromatic amine in the presence of an alkyl- or arylsulfonyl halide to produce the arylidene dye.

The process according to the invention overcomes the limitation of the process that uses the Vilsmeier formylation reaction to produce the required aminobenzaldehyde intermediate. In particular, the process of the present invention allows the preparation of arylidene dyes that contain such substituents as hydroxy, acetamido, and monoalkylsubstituted amino.

The process of the present invention has the advantage over the process of U.S. Pat. No. 4,006,178 in that it does not require the preparation and isolation of a reactive intermediate by a multistep procedure. The process according to the invention has the additional advantage of generating no hydrogen chloride, so that it requires only a stoichiometric amount, not an excess, of the aromatic amine reactant.

DETAILED DESCRIPTION OF THE INVENTION

In the novel process an active methylene compound is first converted to an enolate salt by its reaction with an alkyl formate of low molecular weight, e.g., ethyl formate, in the presence of a strong base such as an alkali metal hydride or alkoxide, e.g., potassium ethoxide, according to the following equation:

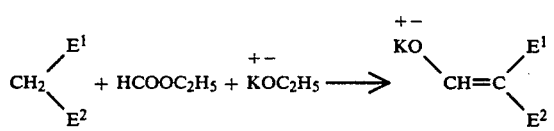

In the second step of the process of the invention the enolate salt reacts with an aromatic amine in the presence of an alkyl- or arylsulfonyl halide, e.g., p-toluenesulfonyl chloride, and preferably a trace amount of pyridine as catalyst, to yield an arylidene dye, according to the following equation:

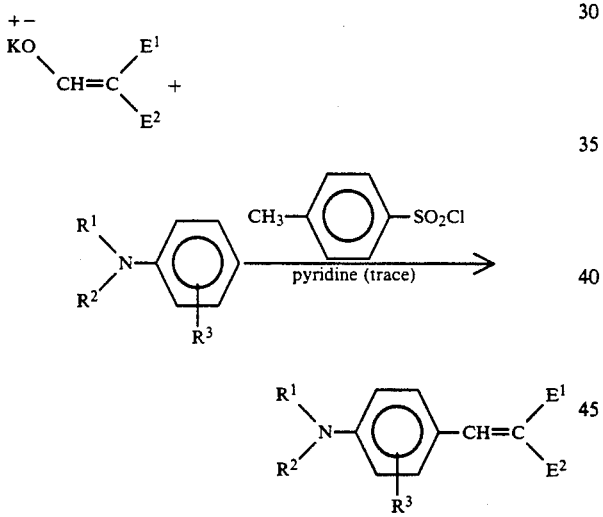

In the above two equations representing the process of the invention, the substituent symbols have the same meanings as stated above in the Brief Summary of the Invention. In the substituents $R^1$, $R^2$, and $R^3$, $E^1$ and $E^2$, "alkyl" and "alk", as in alkoxy and alkanoyl, are lower alkyl groups having, for example, from one to four carbon atoms. The cycloalkyl groups preferably are cyclohexyl. "Aryl" and "ar" refer to phenyl and substituted phenyl. The substituted alkyl and phenyl groups can be substituted with one or more of such groups as hydroxyl; halo, especially chloro; amido; carboxyl; lower alkyl and phenyl.

It is postulated that in the process of the invention an enol sulfonate is a reactive intermediate in the formation of the arylidene dye. The synthesis and isolation of the enol sulfonate has been reported, (*Polymer Bulletin*, 1985, 13,

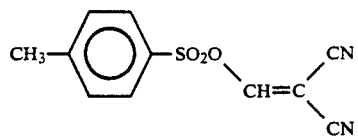

pp. 329-336), but the yield was very low (ca 5%). It is an advantage of the process of the invention that the postulated reactive intermediate is generated in situ and thus does not require isolation. The process is simple to carry out, proceeds under mild conditions, e.g., room temperature, and produces high yields of arylidene dyes. No hydrogen halide is produced, so use of an excess of reactant arylamine is not required for complete reaction. It can be applied to the preparation of dyes with substituents such as hydroxy or acetamido, which cannot be satisfactorily synthesized by previously known methods.

Examples of active methylene compounds that can be used in the process of the invention include the following:

$CH_2(CN)_2$   $CH_2(CONH_2)_2$
$NCCH_2CO_2CH_3$   $NCCH_2CONHC_6H_5$
$NCCH_2CO_2C_2H_5$   $NCCH_2SO_2C_6H_5$

Examples of aromatic amines that can be used in the process of the invention include the following:

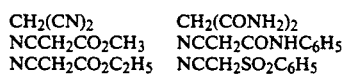

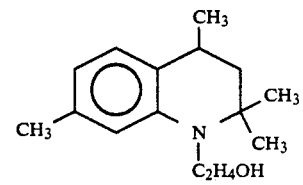

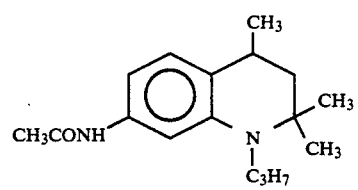

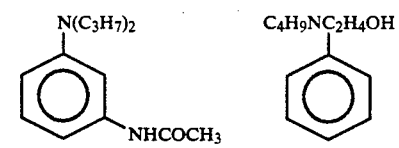

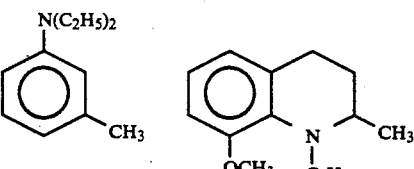

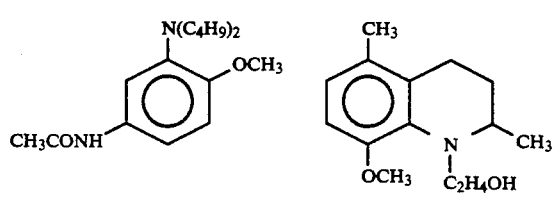

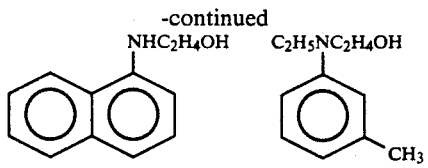

Suitable aromatic amines include compounds that contain substituents such as hydroxy and acetamido that prevent them from being satisfactorily used with previously known methods for producing arylidene dyes.

The sulfonyl halides used in the second step of the process can be lower alkylsulfonyl or arylsulfonyl chlorides, fluorides, or bromides. For reasons of convenience and expense, arylsulfonyl chlorides, e.g., p-toluenesulfonyl chloride, are preferred.

Following are examples of arylidene dyes that can be produced by the process of the invention:

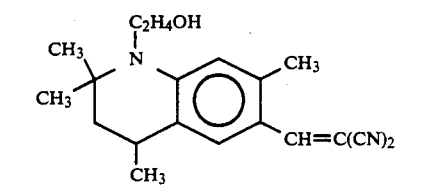

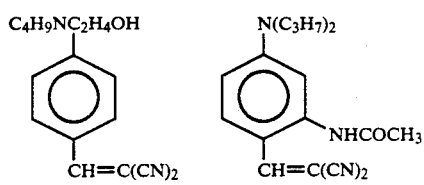

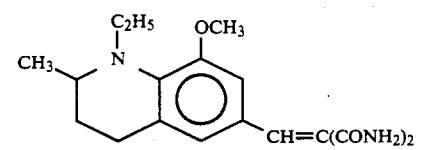

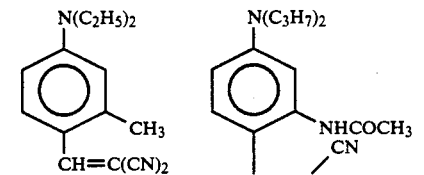

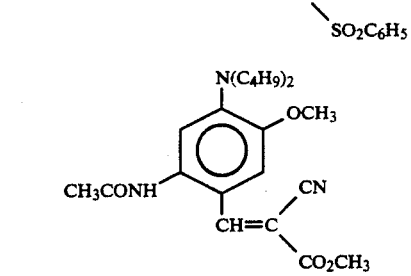

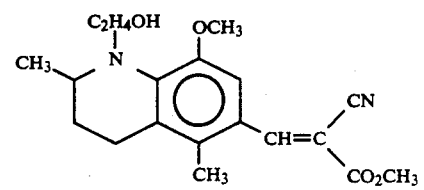

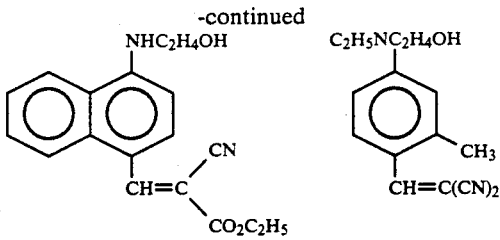

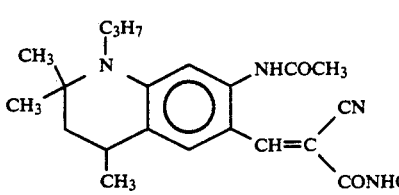

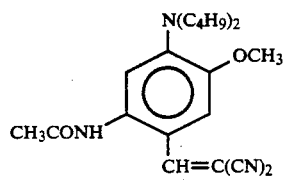

The dyes can be used to dye natural and synthetic textile materials. They can also be blended with plastic materials to serve as colorants and as stabilizers against degradation by ultraviolet radiation. More specifically, such dyes can be sublimed into or otherwise incorporated in polymeric films to form color filters.

The following examples further illustrate the invention:

EXAMPLE 1

Preparation of
1,1-Dicyano-2-(6-(N-hydroxyethyl-2,2,4,7-tetramethyl-tetrahydroquinolinyl))ethylene The potassium salt of hydroxymethylenemalononitrile was prepared by dissolving 23 g (0.21 mole) of potassium t-butoxide in 140 ml of absolute ethanol, adding 13.2 (0.20 mole) of malononitrile and 30 g (0.40 mole) of ethyl formate, and refluxing in mixture for 1.5 hours. The mixture was cooled, and the precipitated product was collected by filtration, washed with ether, and dried in a vacuum desiccator. Yield: 18.1 g (68.5%).

To a stirred mixture of 2.3 g (0.01 mole) of N-hydroxyethyl-2,2,4,7-tetramethyltetrahydroquinoline (prepared as described in *Chemistry and Applications of Dyes*, Waring and Hallas, editors, Plenum, N.Y., 1990, p. 144) and 25 ml of acetonitrile was added 1.3 g (0.01 mole) of the potassium salt of hydroxymethylenemalononitrile, prepared as described above. Then 1.9 g (0.01 mole) of p-toluenesulfonyl chloride was added, and the resulting mixture was stirred at room temperature over the weekend. The mixture was poured into water, and the yellow solid that separated was collected by filtration and dried. The yield was 2.0 g (64%). The solid was recrystallized from 1:1 ethanol-water and then from toluene. Analysis: Calculated for $C_{19}H_{23}N_3O$: C, 73.76; H, 7.49; N, 13.58. Found: C, 73.64; H, 7.31; N, 13.31.

Spectrophotometric measurement of an acetone solution of the recrystallized arylidene dye gave an absorption maximum at 452 nm, with an extinction coefficient of $5.64 \times 10^4$.

This example demonstrates that the process of the invention produces a good yield of arylidene dye from an aromatic amine containing a hydroxy substituent.

EXAMPLE 2

Preparation of 1,1-Dicyano-2-(2-acetamido-4-N,N-dipropylaminophenyl)ethylene

To a solution of 2.34 g (0.01 mole) N,N-dipropyl-m-acetamidoaniline in 25 ml of acetonitrile was added 1.90 (0.01 mole) of p-toluenesulfonyl chloride, followed by three drops of pyridine. To this mixture was added 1.32 g (0.01 mole) of the potassium salt of hydroxymethylenemalononitrile, prepared as described in Example 1. The resulting mixture was stirred at room temperature for two hours, then treated with 75 ml of water. The solid that separated was collected by filtration, washed with water, and dried. The yield of arylidene dye was 2.4 g (77%). Analysis: Calculated for $C_{18}H_{22}N_4O$: C, 69.65; H, 7.14; N, 18.05. Found: C, 69.44; H, 6.97; N, 17.88.

Spectrophotometric measurement of an acetone solution of the arylidene dye gave an absorption maximum at 445 nm, with an extinction coefficient of $5.23 \times 10^4$.

The invention has been described in detail with particular reference to preferred embodiments thereof, but it will be understood that variations and modifications can be effected within the spirit and scope of the invention.

What is claimed :

1. A process for the preparation of an arylidene dye of the formula

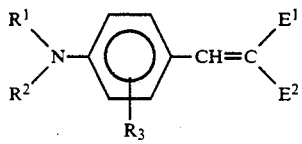

wherein $R^1$ and $R^2$ are hydrogen, alkyl or cycloalkyl, or alkyl or cycloalkyl substituted with hydroxyl, halo, amido, carboxyl or phenyl, $R^3$ is a hydrogen, an alkyl or alkoxy, a phenyl ring fused with the phenyl ring shown, or a alkanoylamino, aroylamino, alkoxycarbonylamino or aryloxycarbonylamino, or $R^2$ and $R^3$ together form a saturated heterocyclic ring, and each of $E^1$ and $E^2$ is —CHNH$_2$ or an unsaturated substituent which is more electron withdrawing than —CONH$_2$, said process comprising reacting an active methylene compound of the structure, $E^1$—CH$_2$—$E^2$, with an alkyl formate in the presence of a storing base to yield a hydroxymethylene enolate salt, and reacting said enolate salt with an aromatic amine of the formula

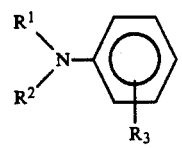

in the presence of an aryl- or alkylsulfonyl halide to yield an arylidene dye.

2. A process of claim 1 wherein
the formylating agent is a lower alkyl formate,
the strong base is an alkali meatal alkoxide or hydride,
and the sulfonyl halide compound is a lower alkylsulfonyl or arylsulfonyl chloride, fluoride, or bromide.

3. A process of claim 2 wherein the active methylene compound is malononitrile.

4. A process of claim 2 wherein the formylating agent is ethyl formate or methyl formate.

5. A process of claim 2 wherein the strong base is potassium ethoxide, sodium methoxide, potassium t-butoxide or sodium hydride.

6. A process of claim 2 wherein the sulfonyl halide compounds is p-toluenesulfonyl chloride, methanesulfonyl chloride, benzenesulfonyl chloride or p-toluenesulfonyl fluoride.

7. A process of claim 1 for the preparation of 1,1-dicyano-2-(6-(N-hydroxyethyl-2,2,4,7-tetramethyl-tetrahydroquinolinyl)ethylene wherein the active methylene compounds is malononitrile and the aromatic amine is N-hydroxyethyl-2,2,4,7,-tetramethyltetrahydroquinoline.

8. A process of claim 1 for the preparation of 1,1-dicyano-2-(2-acetamido-4-N,N-dipropylaminophenyl)ethylene wherein the active methylene compounds is malononitrile and the aromatic amine is N,N-dipropyl-m-acetamidoaniline.

* * * * *

UNITED STATES PATENT AND TRADEMARK OFFICE
CERTIFICATE OF CORRECTION

PATENT NO. : 5,214,186
DATED : May 25, 1993
INVENTOR(S) : L. Shuttleworth

It is certified that error appears in the above-indentified patent and that said Letters Patent is hereby corrected as shown below:

In Column 7, line 48, delete "CHNH$_2$" and insert --CONH$_2$--.

In Column 8, line 5, delete "storing" and insert --strong--.

In Column 8, line 34, delete "compounds" and insert --compound--.

In Column 8, lines 44 and 45, delete "-)ethylene" and insert --)-ethylene--.

In Column 8, line 45, delete "compounds" and insert --compound--.

Signed and Sealed this

Eighth Day of March, 1994

Attest:

BRUCE LEHMAN

Attesting Officer     Commissioner of Patents and Trademarks